(12) United States Patent
Lyu et al.

(10) Patent No.: US 11,160,907 B2
(45) Date of Patent: *Nov. 2, 2021

(54) MEDICAL DEVICE WITH A TUBULAR PORTION COMPRISING A THERMOPLASTIC ELASTOMER WITH SOFT AND HARD SEGMENTS, METHOD FOR PREPARATION THEREOF, AND USE THEREOF

(71) Applicant: MEDTRONIC, INC., Mounds View, MN (US)

(72) Inventors: Suping Lyu, Mounds View, MN (US); XiangJi Chen, Fridley, MN (US); Jing Chen, Zhejiang (CN); Haining Na, Zhejiang (CN); Jin Zhu, Zhejiang (CN)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/091,040

(22) PCT Filed: Mar. 2, 2017

(86) PCT No.: PCT/CN2017/075377
§ 371 (c)(1),
(2) Date: Oct. 3, 2018

(87) PCT Pub. No.: WO2018/157342
PCT Pub. Date: Sep. 7, 2018

(65) Prior Publication Data
US 2019/0111186 A1 Apr. 18, 2019

(51) Int. Cl.
*C08L 75/04* (2006.01)
*A61L 29/04* (2006.01)
(Continued)

(52) U.S. Cl.
CPC ............ *A61L 29/049* (2013.01); *A61L 29/14* (2013.01); *A61M 25/0045* (2013.01);
(Continued)

(58) Field of Classification Search
None
See application file for complete search history.

(56) References Cited

U.S. PATENT DOCUMENTS

| 5,040,544 A | 8/1991 | Lessar et al. |
| 5,589,563 A | 12/1996 | Ward et al. |

(Continued)

FOREIGN PATENT DOCUMENTS

| CN | 1587294 A | 3/2005 |
| CN | 101538358 A | 9/2009 |

(Continued)

OTHER PUBLICATIONS

International Search Report and Written Opinion for International Patent Application No. PCT/CN2017/075376, dated Dec. 1, 2017, 13 pages.

(Continued)

*Primary Examiner* — Kevin S Orwig
(74) *Attorney, Agent, or Firm* — Mueting Raasch Group

(57) ABSTRACT

A medical device, a method for preparation thereof, and use thereof are provided. The medical device comprises a thermoplastic elastomer that is composed of soft segments and hard segments. The method for preparing a medical device comprising a thermoplastic elastomer, comprises forming the thermoplastic elastomer into tubing or other shapes via extrusion, molding, or coating, assembling the tubing or other shapes with other parts including: cables, coils, coated cables, or coated coils, and bonding the tubing, cables, or coils with other components including: other tubing components, cables, coils, sleeves, electrical pulse generator, (Continued)

defibrillation shock generator, electrodes, sensors, or drug release components. The medical device is used for correcting cardiac rhythm, defibrillating, assisting hearts, sensing, stimulating neurological systems, gastrointestinal system, or skeletomuscular tissues or organs.

24 Claims, 4 Drawing Sheets

(51) Int. Cl.
    *A61N 1/05*       (2006.01)
    *A61L 29/14*     (2006.01)
    *A61M 25/00*   (2006.01)

(52) U.S. Cl.
    CPC .............. *A61N 1/05* (2013.01); *C08L 75/04* (2013.01); *A61N 1/0507* (2013.01); *A61N 1/0551* (2013.01); *A61N 1/0563* (2013.01); *C08L 2203/02* (2013.01)

(56) References Cited

U.S. PATENT DOCUMENTS

| | | | |
|---|---|---|---|
| 5,864,001 | A | 1/1999 | Masse et al. |
| 6,537,661 | B1 | 3/2003 | Khong et al. |
| 6,915,168 | B1 | 7/2005 | Benz et al. |
| 9,151,873 | B2 | 10/2015 | Frank et al. |
| 9,574,043 | B2 | 2/2017 | Rudolf et al. |
| 9,926,399 | B2 | 3/2018 | Rudolf et al. |
| 2010/0241208 | A1 | 9/2010 | Pinchuk |
| 2011/0152989 | A1 | 6/2011 | Tan |
| 2014/0121742 | A1 | 5/2014 | Boser et al. |
| 2014/0144580 | A1 | 5/2014 | Desai et al. |
| 2014/0171543 | A1* | 6/2014 | Chang .................... G02B 1/043 523/107 |
| 2016/0113710 | A1 | 4/2016 | Ogle et al. |

FOREIGN PATENT DOCUMENTS

| | | | |
|---|---|---|---|
| CN | 105111404 | A | 12/2015 |
| CN | 105315424 | A | 2/2016 |
| EP | 0833854 | | 4/1998 |
| WO | 97/00901 | | 1/1997 |
| WO | 2010/081132 | | 7/2010 |
| WO | WO 2016/098073 | * | 12/2014 ............. C08G 18/48 |

OTHER PUBLICATIONS

International Search Report and Written Opinion for International Patent Application No. PCT/CN2017/075377, dated Nov. 15, 2017, 13 pages.
Coury et al., "Biomedical Uses of Polyurethanes," Advances in Urethane Science and Technology, 1984; 9:130-168, edited by Kurt C. Frisch and Daniel Klempner, Technomic Publishing Co., Lancaster, Pa.
Szycher, "Structure-Property Relations in Polyurethanes", Szycher's Handbook of Polyurethanes CRC Press, Jul. 13, 2012.
Office Action dated Apr. 20, 2020 from U.S. Appl. No. 16/091,045, 13 pages.
European Search Report from EP Application No. 17898707.9 dated Oct. 28, 2020, 9 pages.
Translation of Office Action from CN Application No. 201780087084.9 dated Feb. 3, 2021, 21 pages.
Office Action from CN Application No. 201780087084.9 dated Feb. 3, 2021, 15 pages.

* cited by examiner

MEDICAL DEVICE WITH A TUBULAR PORTION COMPRISING A THERMOPLASTIC ELASTOMER WITH SOFT AND HARD SEGMENTS, METHOD FOR PREPARATION THEREOF, AND USE THEREOF

This application is the § 371 U.S. National Stage of International Application No. PCT/CN2017/075377, filed 2 Mar. 2017, the disclosure of which is incorporated by reference herein in its entirety.

TECHNICAL FIELD

The present application falls within the field of medical device comprising macromolecular material, relating to a medical device formed from a polyurethane comprising polyolefin soft segments. More particularly, the present application relates to a medical device, a method for preparation thereof, and use thereof.

BACKGROUND ART

A polyurethane is a family of polymeric materials whose chains have soft and hard segments. Because of this unique structure, polyurethane materials have many excellent properties, for example, resistance to low temperature, abrasion resistance, and high stability in biological environment, thus widely used in airspace products, medical devices, coatings, textile and leather.

Polyurethanes can be tailored to produce a range of products from soft and flexible to hard and rigid. They can be extruded, injection molded, compression molded, and solution spun, for example. Thus, polyurethanes are important biomedical polymers, and are used in implantable devices such as artificial hearts, cardiovascular catheters, pacemaker lead insulation, etc.

Commercially available polyurethanes used for implantable applications include BIOSPAN segmented polyurethanes available from Polymer Technology Group of Berkeley, Calif., PELLETHANE segmented polyurethanes available from Dow Chemical, Midland, Mich., and TECOFLEX segmented polyurethanes available from Thermedics, Inc., Woburn, Mass. These polyurethanes and others are described in the article "Biomedical Uses of Polyurethanes," by Coury et al., in Advances in Urethane Science and Technology, 9, 130-168, edited by Kurt C. Frisch and Daniel Klempner, Technomic Publishing Co., Lancaster, Pa. (1984). Typically, polyether polyurethanes exhibit more biostability than polyester polyurethanes, and are therefore generally preferred polymers for use in biological applications.

Polyether polyurethane elastomers, such as PELLETHANE 2363-80A (P80A) and 2363-55D (P55D), which are believed to be prepared from polytetramethylene ether glycol (PTMEG) and 4,4'-diphenylmethane diisocyanate (MDI) extended with 1,4-butanediol (BDO), are widely used for implantable cardiac pacing leads. Pacing leads are insulated wires with electrodes that carry stimuli to tissues and biologic signals back to implanted pulse generators. The use of polyether polyurethane elastomers as insulation on such leads has provided significant advantage over silicone rubber, primarily because of the higher tensile strength and elastic modulus of the polyurethanes.

Currently, polyurethane materials used in medical devices often have the following structures: the soft segments are formed by oligomer polyols such as polytetramethyleneoxide (PTMO), polydimethylsiloxane (PDMS), or aliphatic polycarbonate, while the hard segments are formed by diisocyanate such as 4,4'-diphenylmethane diisocyanate (MDI) or hydrogenated MDI (HMDI), and chain extender such as 1,4-butanediol (BDO). However, during long term use, polyether or polycarbonate polyurethanes may chemically degrade through oxidation, hydrolysis, or enzymatic reactions which could result in material failure, or, under certain conditions, even device failure. For example, polyether polyurethane materials, when used in long term implants, can be oxidized. The oxidation caused by the inflammatory reactions often occurs at the device surface contacting the tissues. It is known as environmental stress cracking. The oxidation reaction that occurs at the device surface contacting certain metallic surface (e.g. cobalt and its alloys) is known as metal ion induced oxidization.

Generally, ether bonds are susceptible to oxidation degradation. Unfortunately, oxidative chemicals are present in the patients' biology. Therefore, the key for solving such a problem is to develop a polyurethane material which is composed of soft segments that are more resistant to oxidation reactions than polyether. A number of polyurethanes with new soft segments have been developed in the past, for example, polycarbonate polyurethane (Carbothane™ by Lubrizol, Bionate™ by DSM, etc.), PDMS polyurethane (ElastEon™ by Biomerics, Pursil™ by DSM, etc.), etc. Those new materials have demonstrated improved resistance to oxidation degradation. However, there are concerns of hydrolysis degradation with them.

Recently, a polyurethane material which is made of polyisobutylene soft segment has shown excellent oxidation and hydrolytic degradation resistance. However, the synthesis of this material requires complicated processes. Production of the material at commercial scale with comparable cost remains an issue. Polyethylene diol has been proposed in the past (M. D. Benz, K. Bonnema, E. Didomenico, C. Hobot, D. Miller, "Medical devices containing segmented polyurethane biomaterials", U.S. Pat. No. 6,915,168). It was assumed that polyurethane made of polyethylene segments would have good resistance to oxidation and hydrolytic reactions. Similar to polyisobutylene polyurethane, synthesis process of polyethylene polyurethane remains a technical challenge, which continues to delay the commercialization of the material.

Therefore, there still is a need to develop an effective method for producing polyolefin diols to make polyurethane materials, so as to provide the identification of materials, particularly polyurethanes, that have the desired stability to oxidation and hydrolysis, and desirable physical properties, as well as good processability, particularly for use in implantable medical devices.

SUMMARY OF THE INVENTION

The present disclosure is an effective method for preparing polyolefin polyurethane. The method consists of two parts. The first part is making polyolefin diols by polymerizing dienes followed by hydrogenation. A second part is making polyurethane materials by using microwave heating. The polyolefin polyurethane made in the present way is expected to have the excellent properties for long term biomedical implant applications.

DISCLOSURE OF THE INVENTION

The objects of the present disclosure can be achieved by the following:

{1} A polyurethane, polyurea, or polyurethane-urea elastomeric composition may be defined as a reaction production of:
1) macrodiols or macrodiamines including hydrogenated polyolefin diols, hydrogenate polyolefin diamines, or a mixture of hydrogenated polyolefin diols, hydrogenated polyolefin diamines, polyether diols, and/or polycarbonate diols, wherein the polyolefin diols or polyolefin diamine that may have 0 to 1000 carbon atoms in the main chain, wherein each carbon atom in the main chain may have 0 to 2 side chains and each side chain may have 0 to 30 carbon atoms,
2) a diisocyanate, and
3) a chain extender {2} The polyurethane, polyurea or polyurethane-urea elastomeric composition according to {1}, characterized in that the number-average molecular weight of the elastomeric composition is $5\times10^3$-$1000\times10^3$ g/mol; the ultimate elongation of the elastomeric composition is 100-1000%; the flexural modulus is 1 to 3,000 MPa; and the ultimate tensile strength of the elastomeric composition is 10-100 MPa.

{3} The polyurethane, polyurea or polyurethane-urea elastomeric composition according to {1}, characterized in that the macrodiol is preferably selected from saturated polybutadiene diol, saturated polyisoprene diol, polybutylene diol, polyethylene diol, polypropylene diol, poly(ethylene-propylene) copolymer diol, polyisobutylene diol, and mixtures thereof;
the diisocyanate is selected from toluene-2,4-diisocyanate (TDI), its isomer or a mixture thereof; 4,4'-diphenylmethane diisocyanate (MDI), hexamethylene diisocyanate, isophorone diisocyanate, methylene bis(cyclohexyl) diisocyante (HMDI), trans-cyclohexane, 1,4-diisocyante (CHDI), p-phenyl diisocyanate, lysine diisocyanate, p-phenyl dimethylene diisocyanate, 1,5-cyclopentane diisocyanate, p-tetramethyl ditoluene diisocyanate, m-tetramethyl ditoluene diisocyanate, hydrogenated forms of the above diisocyanate compounds, and mixtures thereof; wherein MDI is particularly preferred; and
the chain extender is selected from ethylene glycol, 1,3-propylenediol, 1,4-butanediol, 1,4-hexandiol, 1,4-cyclohexanediol, 1,6-henxanediol, 1,8-octanediol, 1,9-nondadiol, 1,10-decanediol, ethylenediamine, propylenediamine, butylenediamine, hexanediamine, cyclohexanediamine, and mixture thereof; wherein 1,4-butandiol is preferred.

{4} The polyurethane, polyurea or polyurethane-urea elastomeric composition according to {3}, characterized in that the macrodiol is hydrogenated polybutadiene diol, or hydrogenated polyisoprene diol.

{5} A method for preparing a polyurethane, polyurea or polyurethane-urea elastomeric composition, comprising the following steps:
(i) preparing diols that have unsaturated bonds followed by hydrogenating the diols to obtain hydrogenated diols, wherein the diols have the following structure:

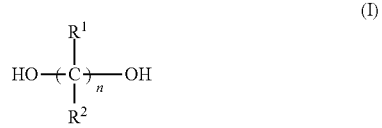

(I)

wherein n is an integer of 1-1000; and, $R^1$ and $R^2$ are independently H, $C_{1-30}$ alkyl, $C_{3-30}$ cycloalkyl or $C_{2-30}$ alkenyl;

(ii) conducting pre-polymerization of the hydrogenated diols obtained in step (i) with a diisocyanate and a polymerization catalyst by using microwave radiation, to obtain a polyurethane prepolymer; and
(iii) adding a chain extender into the polyurethane prepolymer, and continuing a polymerization by using microwave radiation, to obtain the polyurethane.

{6} The method according to {5}, characterized in that in step (i), adding the diols and a noble metal hydrogenating catalyst into a hydrogenating reactor to hydrogenate the diols.

{7} The method according to {6}, characterized in that the reaction temperature is 0-200° C., the reaction pressure is 0.1-100 MPa, and the reaction time is 1-24 h; and, the noble metal hydrogenating catalyst is one of the Pt group metals.

{8} The method according to {5}, characterized in that in step (ii), the diisocyanate is selected from toluene-2,4-diisocyanate (TDI), its isomer or a mixture thereof; 4,4'-diphenylmethane diisocyanate (MDI), hexamethylene diisocyanate, isophorone diisocyanate, methylene bis(cyclohexyl) diisocyante (HMDI), trans-cyclohexane, 1,4-diisocyante (CHDI), p-phenyl diisocyanate, lysine diisocyanate, p-phenyl dimethylene diisocyanate, 1,5-cyclopentane diisocyanate, p-tetramethyl ditoluene diisocyanate, m-tetramethyl ditoluene diisocyanate, and mixtures thereof; the polymerization catalyst is selected from the group consisting of triethylene diamine, dibutyldilaurate tin, stannous octoate, and mixtures thereof; and
the pre-polymerization temperature is 50-200° C., and the pre-polymerization time is 1-5 h; and the microwave radiation power is adjusted such that the temperature is maintained within the intended range, for example, applying 300-600 W for 50 mL to 800 mL of reactant mixture.

{9} The method according to {8}, characterized in that the pre-polymerization temperature is from 65 to 95° C.

{10} The method according to {5}, characterized in that in step (iii), the chain extender is selected from ethylene glycol, 1,3-propylenediol, 1,4-butanediol, 1,4-hexandiol, 1,4-cyclohexanediol, 1,6-henxanediol, 1,8-octanediol, 1,9-nondadiol, 1,10-decanediol, p-diphenyl ethylene diol, colophony dimethol, ethylenediamine, propylenediamine, butylenediamine, hexanediamine, cyclohexanediamine, and mixture thereof; and the polymerization temperature is 50-250° C., and the polymerization time is 2-3 h; and the microwave radiation power is adjusted such that the temperature of the reaction mixture is maintained within the intended range, for example, applying 300-600 W for 50 mL to 800 mL of reactant mixture.

{11} The method according to {10}, characterized in that the pre-polymerization temperature is from 65 to 95° C.

{12} The method according to {5}, characterized in that the steps (i)-(iii) are conducted in the presence of a solvent, wherein the solvent is selected from toluene, xylene, tetrahydrofuran, trichloromethane, N,N-dimethyl formamid, ethyl acetate, N,N-dimethylacetamide, dimethyl sulfoxide and mixtures thereof.

{13} An alternative method to make the same polyurethane, polyurea or polyurethane-urea elastomeric composition includes the following steps: (1) making unsaturated diol by polymerizing dienes, (2) making polyurethane, and (3) hydrogenating the polymer into saturated polyurethane.

{14} A medical device comprising the elastomeric composition according to any one of {1}-{4}.

{15} The medical device according to {14}, characterized in that it is an electrical stimulation device, including: neurological stimulation device, cardiac stimulation device, heart assist device, gastrointestinal stimulation device, skeletomuscular stimulation devices, or sensing devices.

{16} The medical device according to {14}, characterized in that it is an implantable cardia pacing lead, including: coaxial lead, or multilumen lead.

{17} The medical device according to {14}, characterized in that it is an implantable cardioverter defibrillation lead, including: coaxial lead, or multilumen lead.

{18} The medical device according to {14}, characterized in that it is a sensing device, including: electrical sensing, mechanical sensing, or chemical sensing.

{19} The medical device according to {14}, characterized in that it is a combined stimulation lead with sensors.

{20} The medical device according to {14}, characterized in that the thermoplastic elastomer is an insulation layer.

{21} The medical device according to {14}, characterized in that the thermoplastic elastomer is an outside sheath.

{22} The medical device according to {14}, characterized in that the thermoplastic elastomer is a structural component.

{23} The medical device according to {14}, characterized in that the thermoplastic elastomer is a spatial filling component.

{24} The medical device according to {14}, characterized in that the thermoplastic elastomer is a component for jointing other components.

{25} The medical device according to any one of {14}-{24}, comprising: cable of metal wires at the core;
a layer of polymeric insulation materials surrounding the cable of metal wires; another layer of polymeric insulation materials surrounding the layer of polymeric insulation materials;
coil of metal wires surrounding the layer of polymeric insulation materials; and a layer of the elastomeric composition surrounding the coil of metal wires.

{26} The medical device according to any one of {14}-{24}, comprising: coil of metal wires at the core;
a layer of polymeric insulation materials surrounding the coil of metal wires; another layer of polymeric insulation materials surrounding the layer of polymeric insulation materials;
coil of metal wires surrounding the layer of polymeric insulation materials; and a layer of the elastomeric composition surrounding the coil of metal wires.

{27} The medical device according to any one of {14}-{24}, comprising:
a multi-lumen tubing having a plurality of conductor lumens each containing a plurality of coil of metal wires and cable of metal wires, wherein the multi-lumen tubing is made from the elastomeric composition; and
layers of polymeric insulation materials surrounding the coil of metal wires and cable of metal wires.

{28} The medical device according to any one of {14}-{24}, comprising:
a multi-lumen tubing having a plurality of conductor lumens each containing a plurality of coil of metal wires and cable of metal wires, wherein the multi-lumen tubing is made from the elastomeric composition;
an overlay tubing surrounding the multi-lumen tubing; and
layers of polymeric insulation materials surrounding the coil of metal wires and cable of metal wires.

{29} The medical device according to any one of {14}-{24}, characterized in that it is an implantable cardioverter defibrillation lead, wherein
(1) the thermoplastic elastomer is in a shape of tubing with wall thickness from 0.001 inch to 0.030 inch,
(2) one or more than one conductor coils are inserted in the tubing defined in (1), wherein the coils may or may not be coated with additional insulation layer, chemical barrier, mechanical lubricant layer, or the combination thereof,
(3) another insulation material in tubing shape is inserted inside the conductor coils defined in (2), wherein the wall thickness is 0.001 inch to 0.010 inch,
(4) the inner diameter surface of the tubing defined in (3) may or may not have an electrical insulation liner, chemical barrier, mechanical lubricant liner, or the combination thereof, and
(5) electrical conductors are inserted in the tubing defined in (4), wherein the conductors can be cables or coils that can be coated with electrical insulation layer, chemical barrier layer, mechanical lubricant layer, or the combination thereof.

{30} The medical device according to any one of {14}-{24}, characterized in that it is an implantable cardiac pacing lead, wherein
(1) the thermoplastic elastomer is in a shape of tubing with wall thickness from 0.001 inch to 0.030 inch,
(2) one or more than one conductor coils are inserted in the tubing defined in (1), wherein the coils may or may not be coated with insulation layer, chemical barrier, mechanical lubricant layer, or the combination thereof,
(3) another insulation material in tubing shape is inserted inside the conductor coils defined in (2), wherein the wall thickness is 0.001 inch to 0.010 inch,
(4) the inner diameter surface of the tubing defined in (3) may or may not have an insulation liner, chemical barrier, mechanical lubricant liner, or the combination there, and
(5) electrical conductors are inserted in the tubing defined in (4), wherein the conductors can be cables or coils that can be coated with insulation layer, chemical barrier layer, mechanical lubricant layer, or the combination thereof.

{31} The medical device according to any one of {14}-{24}, characterized in that it is an implantable cardioverter defibrillation lead, wherein
(1) the thermoplastic elastomer is in a shape of tubing with wall thickness from 0.001 inch to 0.030 inch,
(2) a polymeric multilumen tubing is inserted in the tubing defined in (1), wherein the multiple lumens may or may not have same diameter and are located in the tubing such that the wall thickness between lumen and lumen and between lumen and the outer diameter of the tubing is 0.001 inch to 0.020 inch,
(3) any of the lumens may or may not have inner insulation liner, chemical barrier, mechanical lubricant liner, or the combination thereof, and
(4) conductor cables, wires, or coils are inserted in some or all the lumens, wherein the cables, wires or coils may or may not have insulation liner, chemical barrier, mechanical lubricant liner, or the combination thereof.

{32} The medical device according to any one of {14}-{24}, characterized in that it is an implantable cardioverter defibrillation lead, wherein
(1) the thermoplastic elastomer is in a shape of multilumen tubing, wherein the multiple lumens may or may not have same diameter and are located in the tubing such that the wall thickness between lumen and lumen and between lumen and the outer diameter of the tubing is 0.001 inch to 0.020 inch,
(2) any of the lumens may or may not have inner insulation liner, chemical barrier, mechanical lubricant liner, or the combination thereof, and
(3) conductor cables, wires, or coils are inserted in some or all of the lumens, wherein the cables, wires or coils may or may not have insulation liner, chemical barrier, mechanical lubricant liner, or the combination thereof.

{33} A method for preparing a medical device, comprising
(I) preparing a polyurethane, polyurea or polyurethane-urea elastomeric composition according to any one of {5}-{12}; and
(II) forming a biomaterial from the elastomeric composition obtained in (I), so as to prepare a medical device.
{34} A method for preparing a medical device, comprising
(I) preparing a polyurethane, polyurea or polyurethane-urea elastomeric composition according to {13}; and
(II) forming a biomaterial from the elastomeric composition obtained in (I), so as to prepare a medical device.
{35} A method for preparing a medical device comprising a thermoplastic elastomer, comprising:
(1) forming the thermoplastic elastomer into tubing or other shapes via extrusion, molding, or coating,
(2) assembling the tubing or other shapes with other parts including: cables, coils, coated cables, or coated coils, and
(3) bonding the tubing, cables, or coils with other components including: other tubing components, cables, coils, sleeves, electrical pulse generator, defibrillation shock generator, electrodes, sensors, or drug release components.
{36} A method for preparing a medical device comprising a thermoplastic elastomer, comprising:
(1) pre-assembling conductors and/or other components,
(2) shaping the thermoplastic elastomer into tubing or other shapes over the pre-assembled component defined in (1) via extrusion, molding, or coating,
(3) assembling the components defined in (2) with other parts including: cables, coils, coated cables, or coated coils, and
(4) bonding the tubing, cables, or coils with other components including: other tubing components, cables, coils, sleeves, electrical pulse generator, defibrillation shock generator, electrodes, sensors, or drug release components.
{37} Use of a medical device comprising a thermoplastic elastomer according to any one of {14}-{24} for correcting cardiac rhythm, defibrillating, assisting hearts, sensing, stimulating neurological systems, gastrointestinal system, or skeletomuscular tissues or organs.
{38} A medical device electrical lead, comprising:
(a) an elongated lead body made from the medical device according to any one of {14}-{28};
(b) one or more of elongated conductors located within the elongated lead body;
(c) an electrode coupled to a distal end of the elongated conductor; and
(d) an electrical connector coupled to a proximal end of the elongated conductor.
{39} A method of using a medical device electrical lead, the method comprising: providing the medical device electrical lead according to {38};
electrically connecting a first end of the medical device electrical lead to an implantable medical device; and
electrically stimulating or sensing a second end of the medical device electrical lead.

Advantageous Effect

The present application provides a production method that provides a feasible path to make saturated polyethylene diol and other polyolefin diols. It is simple and highly efficient. Specifically, it can be realized with lower equipment cost, shorter reaction time, higher yield, fewer byproducts, and lower energy consumption than that with traditional methods. It is suitable for continuous production at large scale.

Products made with this method can be used for medical devices, particularly for implantable medical devices such as a medical device electrical lead.

The present application designs and makes cardiac electrical therapy delivery leads with the polyethylene and branched polyethylene polyurethane materials via hydrogenation followed by microwave polymerization methods. The leads resist to oxidation degradation failure and have same mechanical performance as the leads made of polyether polyurethane.

BEST MODE FOR CARRYING OUT THE INVENTION

Definition of Terminology

Figure 1:
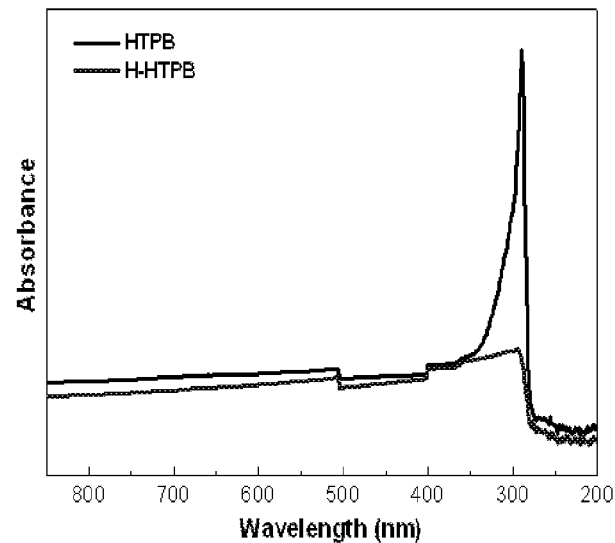
FIG. 1 shows UV absorbance spectrum of polybutylene glycol in Example 1, before hydrogenating vs. after hydrogenating.

In the present application, the terms are defined as follows:

Polymerization is a chemical reaction between many monomers of one or more types. The reaction results in formation of a long chain molecule. The reactive groups of the monomers are chemically linked together and become different groups. For example, a hydroxyl of one monomer and an isocyanate of another monomer can react and form a urethane group. The urethane groups present in the polymer chain and function as linkages.

Diol is an organic compound that has two hydroxyl groups that can react with isocyanate groups of other compounds.

Diisocyanate is an organic compound that has two isocyanate groups that can react with hydroxyl groups to form urethane groups.

Chain extender is a compound that has a molecular weight of less than 200D and two hydroxyl groups that can react with isocyanates. Chain extender can also be diamine or compound with amine at one end and hydroxyl group at the other end, such as 4-amino-1-butanol.

Catalyst is a compound that can accelerate reactions, but is not a part of reaction products.

Unsaturated soft segment diol is a soft segment diol containing C=C double bonds or other unsaturated hydrocarbon bonds.

Hydrogenation is a reaction to convert unsaturated hydrocarbon groups into saturated groups by adding hydrogen atoms, for example converting C=C into C—C. The reaction usually needs hydrogen gas and catalysts.

Polyurethane prepolymer is a polymer that has a molecular weight of 50D to 10,000D and has two isocyanate groups at the ends of each molecule that can react with chain extender to form urethane groups.

Polyurethane is a polymer that is formed through reactions between diol and diisocyanate compounds. Urethane groups formed are the linkages between the monomers.

Chain branch is a chemical group chemically linked to the main chain structure as a side group. A polymer chain can have one or more than one chain branch. Chain braches can be same or different. Some chain branch examples as methyl, ethyl, propyl, butyl, isobutyl, etc.

Microwave radiation reactor is a chemical reactor in which the reaction can proceed under microwave radiation. A typical microwave radiation reactor has non-contact infrared temperature sensors that can be used to monitor reaction mixture temperature and allow the temperature to be controlled on real-time base.

A "biomaterial" may be defined as a material that is substantially insoluble in body fluids and tissues and that is designed and constructed to be placed in or onto the body or to contact fluid or tissue of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; and will substantially maintain its physical properties and function during the time that it remains implanted in or in contact with the body.

An "elastomer" is a polymer that is typically capable of being stretched to approximately twice its original length and retracting to approximately its original length upon release.

A "medical device" may be defined as a device that has surfaces that contact blood or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, stent grafts, medical electrical leads, indwelling catheters, heart valves, and the like, that are implanted in blood vessels or in the heart. This can also include devices for temporary intravascular use such as catheters, guide wires, balloons, and the like which are placed into the blood vessels or the heart for purposes of monitoring or repair.

In one embodiment, the polyurethane cited above can be made in the following way in two steps.

In the first step, making a diol having the following structure:

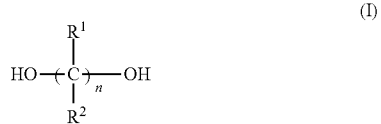

(I)

wherein n is an integer of 1-1000; $R^1$ and $R^2$ are independently H, $C_{1-30}$ alkyl, $C_{3-30}$ cycloalkyl or $C_{2-30}$ alkenyl.

In order to achieve the structure in the first step, a proper diene monomer or a group of proper diene monomers are selected. The diene monomers polymerize alone or copolymerize with other alkene monomers using hydrogen peroxide as catalyst for both cases. The dienes include, but not limited to, butadiene, isoprene, etc. The alkene monomers include, but not limited to, ethylene, propylene, butylene, isobutylene and combination thereof. The molecular weight of polydiene can be controlled by adjusting the ratio of the total double bonds and hydrogen peroxide. The polydienes can also be made by anionic polymerization, living free radical polymerization, and/or other polymerization reactions followed by terminating the two chain ends with hydroxyl groups to form diol structures.

In the second step, the structure (I) made in the first step is hydrogenated into the following saturated diols (II):

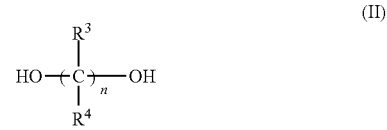

(II)

wherein n is an integer of 1-1000; $R^3$ and $R^4$ are independently H, $C_{1-30}$ alkyl, or $C_{3-30}$ cycloalkyl.

The diols according to the structure (II) is hydrogenated polyethylene diol, hydrogenated polypropylene diol, hydrogenated polybutylene diol, hydrogenated polybutadiene diol, hydrogenated polypentylene diol, hydrogenated poly (4-methyl-1-pentene) diol, hydrogenated polyhexene diol, hydrogenated poly(ethylene-propylene) copolymer diol, or hydrogenated polyisobutylene diol.

During preparing a polyurethane, water and/or other impurities are removed before conducting hydrogenation to avoid poisoning the hydrogenation catalysts. An expert in the field should know methods of removing impurities. One method can be heating the mixtures while applying vacuum for proper duration.

In the first aspect, the present invention provides a medical device comprising a biomaterial formed from a polyurethane, polyurea, or polyurethane-urea elastomer being made of a soft segment diols or diamines including, but not limited to, saturated hydrogenated polyolefin diols, hydrogenated polyolefin diamines, or a mixture of hydrogenated polyolefin diols, hydrogenated polyolefin diamines, polyether diols, and/or polycarbonate diols. The polyolefin diols or polyolefin diamine that may have 0 to 1000 carbon atoms in the main chain, wherein each carbon atom in the main chain may have 0 to 2 side chains and each side chain can have 0 to 30 carbon atoms.

In this invention, the number-average molecular weight of the elastomer is $5 \times 10^3$-$1,000 \times 10^3$ g/mol, preferably $100 \times 100 \times 10^3$-$600 \times 10^3$ g/mol; the ultimate elongation of the elastomer is 100-1000%; the Young's modulus of the elastomer is 1 to 3,000 MPa; and the ultimate tensile strength of the elastomer is 10-100 MPa.

In this invention, the medical device may have the following structure, comprising:
cable of metal wires at the core;
a layer of polymeric insulation materials surrounding the cable of metal wires;
another layer of polymeric insulation materials surrounding the layer of polymeric insulation materials;
coil of metal wires surrounding the layer of polymeric insulation materials; and
a layer of the elastomeric composition surrounding the coil of metal wires.

In this invention, the medical device may have the following structure, comprising:
coil of metal wires at the core;

a layer of polymeric insulation materials surrounding the coil of metal wires;
another layer of polymeric insulation materials surrounding the layer of polymeric insulation materials;
coil of metal wires surrounding the layer of polymeric insulation materials; and
a layer of the elastomeric composition surrounding the coil of metal wires.

In this invention, the medical device may have the following structure, comprising:
a multi-lumen tubing having a plurality of conductor lumens each containing a plurality of coil of metal wires and cable of metal wires, wherein the multi-lumen tubing is made from the elastomeric composition; and
layers of polymeric insulation materials surrounding the coil of metal wires and cable of metal wires.

In this invention, the medical device may have the following structure, comprising:
a multi-lumen tubing having a plurality of conductor lumens each containing a plurality of coil of metal wires and cable of metal wires, wherein the multi-lumen tubing is made from the elastomeric composition;
an overlay tubing surrounding the multi-lumen tubing; and
layers of polymeric insulation materials surrounding the coil of metal wires and cable of metal wires.

In this invention, the metal wire may include, but not limited to: MP35N, Ag cored MP35N, Ta, and low Ti MP35N; and, the polymeric insulation material may include, but not limited to: fluoropolymer, silicone and polyimide.

In this invention, the medical device is an electrical stimulation device, including but not limited to: neurological stimulation device, cardiac stimulation device, heart assist device, gastrointestinal stimulation device, skeletomuscular stimulation devices, sensing devices, etc.

In this invention, the medical device is an implantable cardia pacing lead, including but not limited to: coaxial lead, multilumen lead, etc.

In this invention, the medical device is an implantable cardioverter defibrillation lead, including but not limited to: coaxial lead, multilumen lead, etc.

In this invention, the medical device is a sensing device, including but not limited to: electrical sensing, mechanical sensing, chemical sensing, etc.

In this invention, the medical device is a combined stimulation lead with sensors.

In this invention, the elastomer is an insulation layer.
In this invention, the elastomer is an outside sheath.
In this invention, the elastomer is a structural component.
In this invention, the elastomer is a spatial filling component.
In this invention, the elastomer is a component for jointing other components.

In this invention, the medical device is an implantable cardioverter defibrillation lead, wherein
(1) the thermoplastic elastomer is in a shape of tubing with wall thickness from 0.001 inch to 0.030 inch,
(2) one or more than one conductor coils are inserted in the tubing defined in (1), wherein the coils may or may not be coated with additional insulation layer, chemical barrier, mechanical lubricant layer, or the combination thereof,
(3) another insulation material in tubing shape is inserted inside the conductor coils defined in (2), wherein the wall thickness is 0.001 inch to 0.010 inch,
(4) the inner diameter surface of the tubing defined in (3) may or may not have an electrical insulation liner, chemical barrier, mechanical lubricant liner, or the combination thereof, and
(5) electrical conductors are inserted in the tubing defined in (4), wherein the conductors can be cables or coils that can be coated with electrical insulation layer, chemical barrier layer, mechanical lubricant layer, or the combination thereof.

In this invention, the medical device is an implantable cardiac pacing lead, wherein
(1) the thermoplastic elastomer is in a shape of tubing with wall thickness from 0.001 inch to 0.030 inch,
(2) one or more than one conductor coils are inserted in the tubing defined in (1), wherein the coils may or may not be coated with insulation layer, chemical barrier, mechanical lubricant layer, or the combination thereof,
(3) another insulation material in tubing shape is inserted inside the conductor coils defined in (2), wherein the wall thickness is 0.001 inch to 0.010 inch,
(4) the inner diameter surface of the tubing defined in (3) may or may not have an insulation liner, chemical barrier, mechanical lubricant liner, or the combination there, and
(5) electrical conductors are inserted in the tubing defined in (4), wherein the conductors can be cables or coils that can be coated with insulation layer, chemical barrier layer, mechanical lubricant layer, or the combination thereof.

In this invention, the medical device is an implantable cardioverter defibrillation lead, wherein
(1) the thermoplastic elastomer is in a shape of tubing with wall thickness from 0.001 inch to 0.030 inch,
(2) a polymeric multilumen tubing is inserted in the tubing defined in (1), wherein the multiple lumens may or may not have same diameter and are located in the tubing such that the wall thickness between lumen and lumen and between lumen and the outer diameter of the tubing is 0.001 inch to 0.020 inch,
(3) any of the lumens may or may not have inner insulation liner, chemical barrier, mechanical lubricant liner, or the combination thereof, and
(4) conductor cables, wires, or coils are inserted in some or all the lumens, wherein the cables, wires or coils may or may not have insulation liner, chemical barrier, mechanical lubricant liner, or the combination thereof.

In this invention, the medical device is is an implantable cardioverter defibrillation lead, wherein
(1) the thermoplastic elastomer is in a shape of multilumen tubing, wherein the multiple lumens may or may not have same diameter and are located in the tubing such that the wall thickness between lumen and lumen and between lumen and the outer diameter of the tubing is 0.001 inch to 0.020 inch,
(2) any of the lumens may or may not have inner insulation liner, chemical barrier, mechanical lubricant liner, or the combination thereof, and
(3) conductor cables, wires, or coils are inserted in some or all of the lumens, wherein the cables, wires or coils may or may not have insulation liner, chemical barrier, mechanical lubricant liner, or the combination thereof.

In the second aspect, the present invention provides a method for preparing a medical device, comprising:
(I) preparing the above polyurethane, comprising the following steps:
(i) hydrogenating diol to obtain a hydrogenated diol;
(ii) conducting pre-polymerization of the hydrogenated diol obtained in step (i) with a diisocyanate and a polymerization catalyst by using microwave radiation, to obtain a polyurethane prepolymer; and
(iii) adding a chain extender into the polyurethane prepolymer, and continuing a polymerization by using microwave radiation, to obtain the polyurethane; and (II) forming an elastomeric composition from the polyurethane obtained in (I), so as to prepare a medical device.

In this invention, in step (i), adding diols and a solvent into a reactor, for example, a hydrogenating reactor; after diol is dissolved, adding a noble metal hydrogenating catalyst and hydrogen gas into the reactor; controlling the temperature and pressure to be within pre-planned ranges and letting the reaction continue until completion; and, separating the hydrogenating diols, purifying, and drying them.

In this invention, in step (i), the volume of the hydrogenating reactor is 1-3 L, the reaction temperature is 0-200° C., preferably 50-150° C., the reaction pressure is 0.1-100 MPa, and the reaction time is 1-24 h; and, the noble metal hydrogenating catalyst is one of the Pt group metals (i.e. Ru, Rh, Pd, Os, Ir and Pt) carrier catalysts.

In this invention, in step (ii), before conducting pre-polymerization, heating and dehydrating the hydrogenated soft segment obtained in step (i) in vacuum, wherein the temperature of heating and dehydrating is 80-120° C., and the time of heating and dehydrating is 1-6 h.

In this invention, in step (ii), the diisocyanate is selected from toluene-2,4-diisocyanate (TDI), its isomer or a mixture thereof; 4,4'-diphenylmethane diisocyanate (MDI), hexamethylene diisocyanate, isophorone diisocyanate, methylene bis(cyclohexyl) diisocyante (HMDI), trans-cyclohexane, 1,4-diisocyante (CHDI), p-phenyl diisocyanate, lysine diisocyanate, p-phenyl dimethylene diisocyanate, 1,5-cyclopentane diisocyanate, p-tetramethyl ditoluene diisocyanate, m-tetramethyl ditoluene diisocyanate, and mixtures thereof.

In this invention, in step (ii), the polymerization catalyst is selected from the group consisting of triethylene diamine, dibutyldilaurate tin, stannous octoate, and mixtures thereof.

In this invention, in step (ii), the pre-polymerization temperature is 50-200° C., preferably from 65 to 95° C., and the pre-polymerization time is 1-5 h.

In this invention, in step (ii), the microwave radiation power is 100-800 W for 10 mL to 2 L of reactant mixture.

In this invention, in step (iii), the chain extender is selected from ethylene glycol, 1,3-propylenediol, 1,4-butanediol, 1,4-hexandiol, 1,4-cyclohexanediol, 1,6-henxanediol, 1,8-octanediol, 1,9-nondadiol, 1,10-decanediol, p-diphenyl ethylene diol, colophony dimethol, ethylenediamine, propylenediamine, butylenediamine, hexanediamine, cyclohexanediamine, and mixture thereof;

In this invention, in step (iii), the polymerization temperature is 50-250° C., and the polymerization time is 1-5 h, preferably 2-3 h.

In this invention, the steps (i)-(iii) are conducted in the presence of a solvent, wherein the solvent is selected from the group consisting of toluene, xylene, tetrahydrofuran, trichloromethane, N,N-dimethyl formamid, ethyl acetate, N,N-dimethylacetamide, dimethyl sulfoxide and mixtures thereof.

In this invention, the method comprises:
(1) forming the thermoplastic elastomer into tubing or other shapes via extrusion, molding, coating, etc.,
(2) assembling the tubing or other shapes with other parts including but not limited to: cables, coils, coated cables, coated coils, etc., and
(3) bonding the tubing, cables, coils, etc. with other components including but not limited to: other tubing components, cables, coils, sleeves, electrical pulse generator, defibrillation shock generator, electrodes, sensors, drug release components, etc.

In this invention, the method comprises:
(1) pre-assembling conductors and/or other components,
(2) shaping the thermoplastic elastomer into tubing or other shapes over the pre-assembled component defined in (1) via extrusion, molding, coating, etc.,
(3) assembling the components defined in (2) with other parts including but not limited to: cables, coils, coated cables, coated coils, etc., and
(4) bonding the tubing, cables, coils, etc. with other components including but not limited to: other tubing components, cables, coils, sleeves, electrical pulse generator, defibrillation shock generator, electrodes, sensors, drug release components, etc.

In the third aspect, the present invention provides a medical device electrical lead, comprising:
(a) an elongated lead body made from the above medical device;
(b) one or more of elongated conductors located within the elongated lead body;
(c) an electrode coupled to a distal end of the elongated conductor; and
(d) an electrical connector coupled to a proximal end of the elongated conductor.

In the fourth aspect, the present invention provides a method of using a medical device electrical lead, the method comprising:
providing the above medical device electrical lead;
electrically connecting a first end of the medical device electrical lead to an implantable medical device; and
electrically stimulating or sensing a second end of the medical device electrical lead.

In the fifth aspect, the present invention provides use of the medical device for correcting cardiac rhythm, defibrillating, assisting hearts, sensing, stimulating neurological systems, gastrointestinal system, skeletomuscular tissues or organs, etc.

Figure 3:
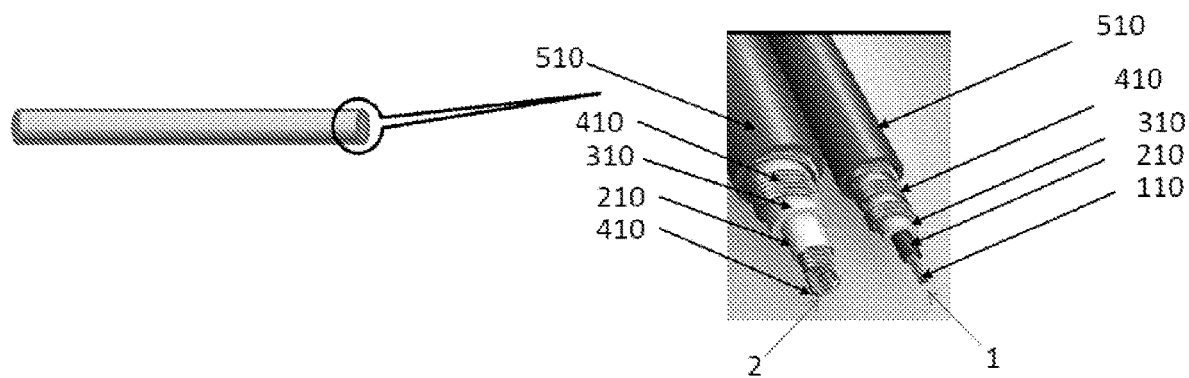
FIG. 3 shows two designs of lead body according to the embodiments of the present application.

With reference to FIG. 3, it shows two designs of lead body according to the embodiments of the present application. The cable design is generalized as the reference sign 1, which comprises: cable of metal wires 110 at the core; a layer of polymeric insulation materials 210 surrounding the cable of metal wires 110; another layer of polymeric insulation materials 310 surrounding the layer of polymeric insulation materials 210; coil of metal wires 410 surrounding the layer of polymeric insulation materials 310; and a layer of the biomaterial 510 surrounding the coil of metal wires 410. The coin design is generalized as the reference sign 2, which comprises: coil of metal wires 410 at the core; a layer of polymeric insulation materials 210 surrounding the coil of metal wires 410; another layer of polymeric insulation materials 310 surrounding the layer of polymeric insulation materials 210; coil of metal wires 410 surrounding the layer of polymeric insulation materials 310; and a layer of the biomaterial 510 surrounding the coil of metal wires 410. This tubing may have OD of 0.8-2 mm, nominal 1.4 mm; wall thickness of 0.08-0.2 mm, nominal 0.1 mm; and material rigidity (Shore Durometer) of 50A-75D, preferably 80A-55D, nominal 55D. This tubing can be made with extrusion process.

Figure 4:
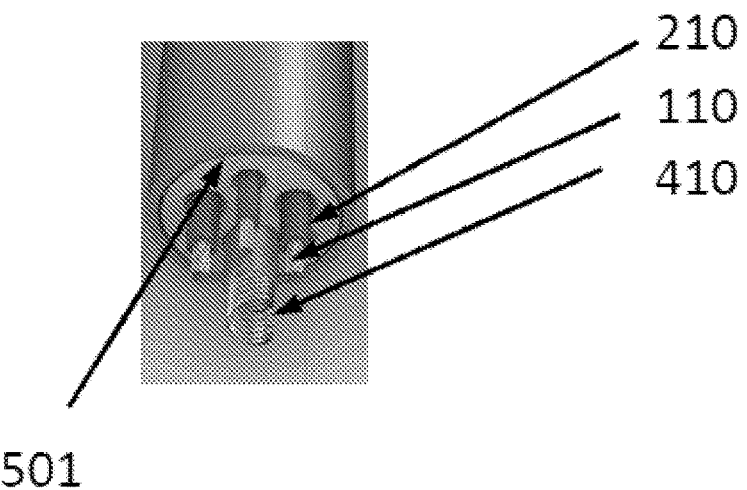
FIG. 4 shows another design of lead body according to the embodiment of the present application.

With reference to FIG. 4, it shows another design of lead body according to the embodiment of the present application, comprising: a multi-lumen tubing 501 having a plurality of conductor lumens each containing a plurality of coil of metal wires 410 and cable of metal wires 110, wherein the multi-lumen tubing 501 is made from the biomaterial; and layers of polymeric insulation materials 210 surrounding the coil of metal wires 410 and cable of metal wires 110.

Figure 5:
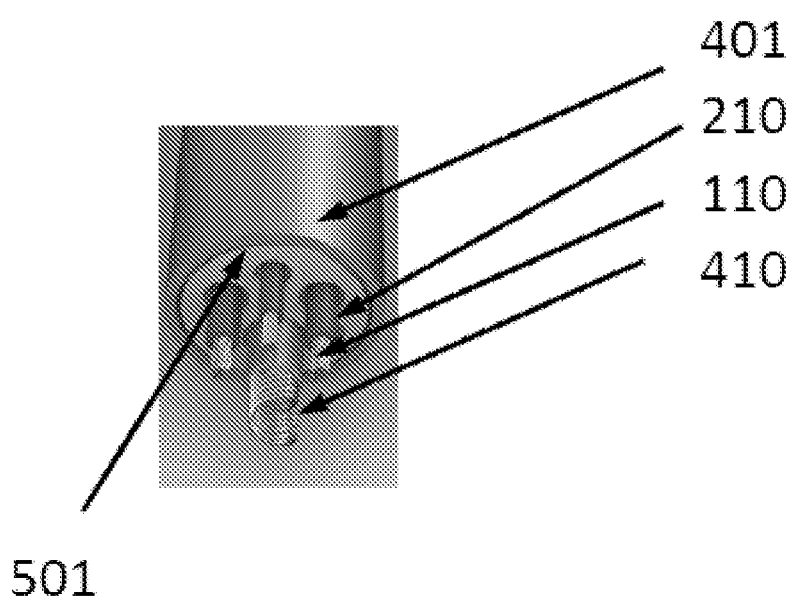
FIG. 5 shows another design of lead body according to the embodiment of the present application.

With reference to FIG. 5, it shows another design of lead body according to the embodiment of the present application, comprising: a multi-lumen tubing 501 having a plurality of conductor lumens each containing a plurality of coil of metal wires 410 and cable of metal wires 110, wherein the multi-lumen tubing 501 is made from the biomaterial; an overlay tubing 401 surrounding the multi-lumen tubing 501; and layers of polymeric insulation materials 210 surrounding the coil of metal wires 410 and cable of metal wires 110.

Figure 6:
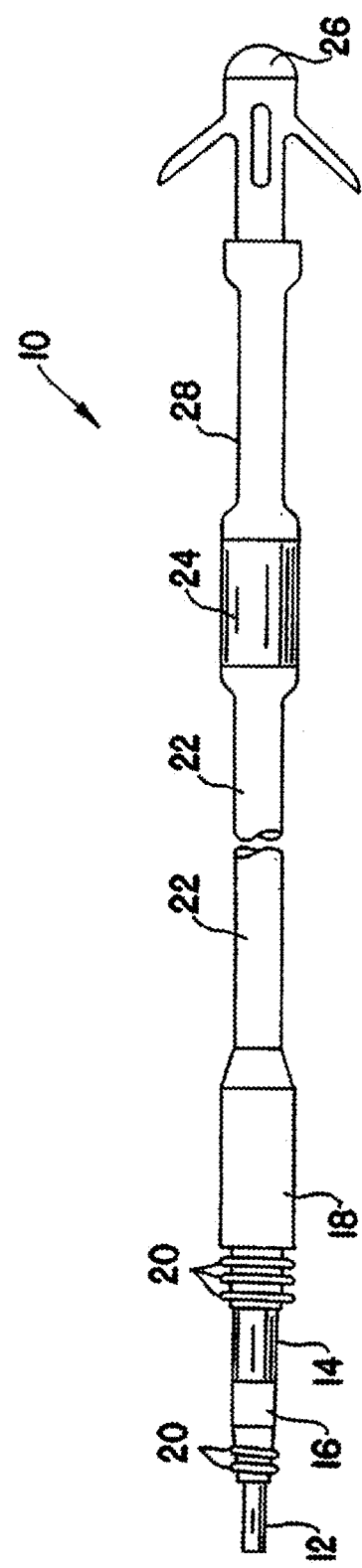
FIG. 6 is a plan view of the medical device electrical lead according to the embodiment of the present application.

With reference to FIG. 6, it is a plan view of the medical device electrical lead according to the embodiment of the present application. As shown in FIG. 6, the pacing lead 10 includes a connector assembly at its proximal end, including a first conductive surface 12, a second conductive surface 14, and two insulative segments 16 and 18; insulative segments 16 and 18 are each provided with a plurality of sealing rings 20; extending from the connector assembly is an elongated lead body, including an outer insulative sheath 22, which is formed from the polymers described above; within insulative sheath 22 is located an elongated conductor (not shown), such as a quadrifilar, multiconductor coil, which is described in U.S. Pat. No. 5,040,544 (Lessar et al.); two of the conductors within the coil are coupled to conductive surface 12, and the other two are coupled to conductive surface 14; at the distal end of the lead are located a ring electrode 24, coupled to two of the conductors, and a tip electrode 26, coupled to the other two of the four conductors of the quadrifilar coil; and, extending between ring electrode 24 and tip electrode 26 is an additional insulative sheath 28. Such medical electrical leads can be implanted into a vein or artery of a mammal and electrically connected to an implantable medical device.

The invention has been described with reference to various specific and preferred embodiments and will be further described by reference to the following detailed Examples. It is understood, however, that there are many extensions, variations, and modification on the basic theme of the present invention beyond that shown in the examples and detailed description, which are within the spirit and scope of the present invention.

EXAMPLES

Examples are given below in order to specifically describe the present invention; however, the present invention is not limited to the examples that are described below. In the following examples, measurements or quantity ratios are based on weight in all instances.

Example 1: Preparing Hydrogenated Diols 50 g of polybutadiene diol and 600 mL THF were added into a hydrogenating kettle; after polybutadiene diol was dissolved, 12 g of Pt hydrogenating catalyst and hydrogen gas were added into the hydrogenating kettle; the temperature was controlled to be 60° C. and pressure was controlled to be 2 MPa and the reaction continued for 20 hours until completion; and, the obtained hydrogenated diols were separated, purified, and dried.

Example 2

Procedure:
30 mL toluene and 3.7 g hydrogenated polybutadiene diol (H-HTPB) were added in a 100 mL glass reactor. The mixture was stirred until the H-HTPB was dissolved in the toluene. Then 1.5 g 4,4'-diphenyl methane diisocyanate was added followed by adding 40 μL dibutyldilaurate tin catalyst. Microwave radiation (400 W) was then used to heat the reaction mixture to maintain its temperature at 65° C. while it was stirred. After 2 hours of reaction, 0.36 g of chain extender BDO (calculated according to the amount of titrated isocyanate such that the total molar of OH is equal to that of isocyanate); and then the temperature was raised to 80° C. by increasing microwave power to 500 W. Let the reaction continue for 2 more hours. When the isocyanate completely reacted based on FI-IR test, the reaction was stopped. The reaction solution was poured into menthol to precipitate the polymer product. The mixture was placed in a refrigerator for 24 hours. The solid polymer product was harvested by centrifuging mixture. The product was dried in vacuum oven for 24 hours.

Result:
The yield of the reaction was 75%. The number-average and weight-average molecular weights measured with Gel Permeation Chromatography (GPC) were $Mn=30\times10^3$ g/mol, and $Mw=50\times10^3$ g/mol.

FIG. 1 shows UV absorbance spectrum of polybutylene glycol before hydrogenating vs. after hydrogenating. The characteristic absorbance peak of double bond of HTPB at 288 nm disappeared after hydrogenating, indicating that all of the double bond in HTPB were hydrogenated.

Figure 2:
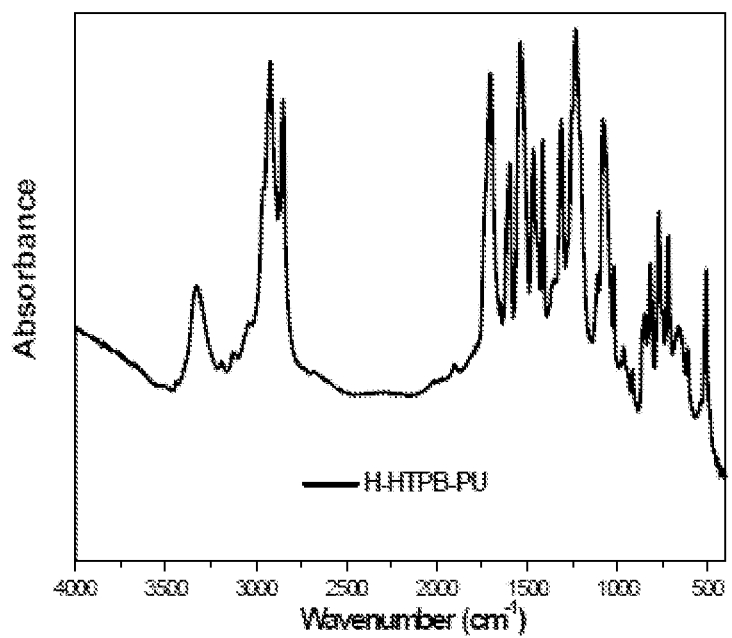
FIG. 2 shows IR spectrum of the obtained polyurethane in Example 1.

FIG. 2 shows IR spectrum of the resulting polyurethane. The characteristic peak of isocyanate group —NCO at 2,270 $cm^{-1}$ disappeared, indicating that all of the residual isocyanate groups had been reacted in the last step. The peaks at 3,327 $cm^{-1}$ and 1,538 $cm^{-1}$ were assigned to —NH— of the urethane group and the peak at 1,710 $cm^{-1}$ was assigned to —C=O of urethane group. These two peaks suggest the formation of urethane.

Example 3

Procedure:
30 mL toluene was added in a 100 mL glass reactor and heated to 65° C. 3.7 g hydrogenated polybutadiene diol (H-HTPB) was added in the reactor. The mixture was stirred until the H-HTPB was dissolved in the toluene. Then 1.5 g 4,4'-diphenyl methane diisocyanate was added followed by adding 40 μL dibutyldilaurate tin catalyst. The reaction mixture was heated with a regular heater to maintain its temperature at 65° C. while it was stirred. After 5 hours of reaction, 0.36 g of chain extender BDO (calculated according to the amount of titrated isocyanate such that the total molar of OH is equal to that of isocyanate); and then the temperature was raised to 80° C. by increasing heating power. Let the reaction continue for 5 more hours. When the isocyanate completely reacted based on FI-IR test, the reaction was stopped. The reaction solution was poured into menthol to precipitate the polymer product. The mixture was placed in a refrigerator for 24 hours. The solid polymer product was harvested by centrifuging mixture. The product was dried in vacuum oven for 24 hours.

Result:
The yield of the reaction was 70%, and the number-average and weight-average molecular weights measured by Gel Permeation Chromatography (GPC) were $Mn=15\times10^3$ g/mol, and $Mw=30\times10^3$ g/mol.

Example 4: Mechanical Test (GB/T 528-2009)

Test Condition:
Instrument: Instron 5567 Electric Universal Testing Machine (Instron, America);

Gauge length: 50 mm; Cross-head speed: 5 mm min$^{-1}$. The specimens of 35 mm×2 mm×0.5 mm were used for this evaluation.

The data was taken from an average of at least five specimens for accuracy.

Result:

The mechanical properties of polyurethane include follows:

In Example 2, ultimate elongation of polyurethane is 500%; Young's modulus is 380 MPa; and ultimate tensile strength is 33 MPa.

In Example 3, ultimate elongation of polyurethane is 70%; Young's modulus is 25 MPa; and ultimate tensile strength is 10 MPa.

APPLICABILITY

In this invention, the time for synthesizing the polyolefin polyurethane under microwave radiation is no more than 5 h, while the reaction time of the traditional heating manner is around 10 h. The microwave radiation greatly shortens the reaction time, and lowers energy consumption, providing a high-efficient and environment friendly route for synthesizing the polyolefin polyurethane. The industrial applicability covers almost all potential use of the polyolefin polyurethane, particularly for implantable medical devices such as a medical device electrical lead.

The invention claimed is:

1. A medical device comprising:
an extruded or molded shape prepared from a thermoplastic elastomer by extruding or injection molding the thermoplastic elastomer, the thermoplastic elastomer comprising soft segments and hard segments, wherein
the soft segments are made of saturated polyolefin diols or polyolefin diamine, the saturated polyolefin diols or polyolefin diamine having 2 to 1000 carbon atoms in a main chain, wherein each carbon atom in the main chain may have 0 to 2 side chains and each side chain may have 0 to 30 carbon atoms,
the hard segment is made of a diisocyanate and a chain extender,
the hard segments make up 10-60% of the elastomer and the soft segments make up the rest,
wherein the thermoplastic elastomer is made by exposing a polymerization mixture prepared from the saturated polyolefin diols or polyolefin diamine, the diisocyanate, and the chain extender to microwave radiation, and
wherein the number-average molecular weight of the elastomer is 5×10$^3$-1000×10$^3$ g/mol; the ultimate elongation of the elastomer is 100-1000%; the Young's modulus of the elastomer is 10 to 3,000 MPa; and the ultimate tensile strength of the elastomer is 10-100 MPa.

2. The medical device of claim 1, wherein the number-average molecular weight of the elastomer is 10×10$^3$-300×10$^3$ g/mol; the ultimate elongation of the elastomer is 200-700%; the Young's modulus of the elastomer is 10 to 2,000 MPa; and the ultimate tensile strength of the elastomer is 10-100 MPa.

3. The medical device of claim 1, wherein the soft segment is formed from saturated polybutadiene diol, saturated polyisoprene diol, polybutylene diol, polyethylene diol, polypropylene diol, poly(ethylene-propylene) copolymer diol, polyisobutylene diol, branched polyethylene diol, polybutylene diamine, polyethylene diamine, polypropylene diamine, poly(ethylene-propylene) copolymer diamine, saturated polybutadiene, saturated polyisoprene diamine, saturated polyisobutylene diamine, branched polyethylene diamine, or a mixture thereof.

4. The medical device of claim 1, wherein the diisocyanate is selected from toluene-2,4-diisocyanate, its isomer or a mixture thereof; 4,4'-diphenylmethane diisocyanate, hexamethylene diisocyanate, isophorone diisocyanate, 4,4'-dicyclohexylmethane diisocyanate, methylene bis(cyclohexyl) diisocyanate, trans-cyclohexane, 1,4-diisocyante, p-phenyl diisocyanate, lysine diisocyanate, p-phenyl dimethylene diisocyanate, 1,5-cyclopentane diisocyanate, p-tetramethyl ditoluene diisocyanate, m-tetramethyl ditoluene diisocyanate, hydrogenated forms of the preceding diisocyanate compounds, and mixtures thereof.

5. The medical device of claim 1, wherein the chain extender is selected from ethylene glycol, 1,3-propylenediol, 1,4-butanediol, 1,4-hexanediol, 1,4-cyclohexanediol, 1,6-henxanediol, 1,8-octanediol, 1,9-nondadiol, 1,10-decanediol, ethylenediamine, propylenediamine, butylenediamine, hexanediamine, cyclohexanediamine, and mixtures thereof.

6. The medical device of claim 3, wherein the soft segment is hydrogenated polybutadiene diol.

7. The medical device of claim 3, wherein the soft segment is hydrogenated polyisoprene diol.

8. The medical device of claim 1, wherein the medical device is an electrical stimulation device comprising a neurological stimulation device, a cardiac stimulation device, a heart assist device, a gastrointestinal stimulation device, a skeletomuscular stimulation device, or a sensing device.

9. The medical device of claim 8, wherein the medical device is an implantable cardia pacing lead comprising a coaxial lead or a multilumen lead.

10. The medical device of claim 8, wherein the medical device is an implantable cardioverter defibrillation lead comprising a coaxial lead or a multilumen lead.

11. The medical device of claim 1, wherein the medical device is a sensing device comprising an electrical sensing device, mechanical sensing device, or chemical sensing device.

12. The medical device of claim 1, wherein the medical device is a combined stimulation lead with sensors.

13. The medical device of claim 1, wherein the medical device is an insulation layer.

14. The medical device of claim 1, wherein the medical device is an outside sheath.

15. The medical device of claim 1, wherein the medical device is a structural component.

16. The medical device of claim 1, wherein the medical device is a spatial filling component.

17. The medical device of claim 1, wherein the medical device is a component for jointing other components.

18. The medical device of claim 1, wherein the medical device is an implantable cardioverter defibrillation lead, wherein
the thermoplastic elastomer forms a first tubing with wall thickness from 0.001 inch to 0.030 inch,
one or more conductor coils are disposed inside the first tubing,
a second insulation material forms a second tubing disposed inside the conductor coils, wherein the second tubing has a wall thickness of 0.001 inch to 0.010 inch, and
electrical conductors are disposed in the second tubing.

19. The medical device of claim 1 comprising an implantable cardiac pacing lead, wherein the thermoplastic elastomer forms a first tubing with wall thickness from 0.001 inch to 0.030 inch, one or more conductor coils are disposed inside the first tubing a second insulation material forms a second tubing disposed inside the conductor coils, wherein the second tubing has a wall thickness of 0.001 inch to 0.010 inch, and electrical conductors are disposed in the second tubing.

20. The medical device of claim 1 comprising an implantable cardioverter defibrillation lead, wherein the thermoplastic elastomer forms a first tubing with wall thickness from 0.001 inch to 0.030 inch, a polymeric multilumen tubing comprising multiple lumens is inserted in the first tubing, wherein the multiple lumens are located in the multilumen tubing such that wall thickness between lumen and lumen and between lumen and an outer diameter of the multilumen tubing is 0.001 inch to 0.020 inch, and conductor cables, wires, or coils are inserted in some or all the lumens.

21. The medical device of claim 1 comprising an implantable cardioverter defibrillation lead, wherein the thermoplastic elastomer forms a multilumen tubing comprising multiple lumens, wherein the multiple lumens are located in the multilumen tubing such that wall thickness between lumen and lumen and between lumen and an outer diameter of the multilumen tubing is 0.001 inch to 0.020 inch, and conductor cables, wires, or coils are inserted in some or all of the lumens.

22. A method for preparing the medical device of claim 1 comprising a thermoplastic elastomer, comprising:

forming the thermoplastic elastomer into tubing or other shapes via extrusion or injection molding, assembling the tubing or other shapes with one or more other parts comprising cables, coils, coated cables, or coated coils, and bonding the tubing, cables, or coils with one or more other components comprising other tubing components, cables, coils, sleeves, electrical pulse generator, defibrillation shock generator, electrodes, sensors, or drug release components.

23. A method for preparing the medical device of claim 1 comprising a thermoplastic elastomer, comprising:

pre-assembling conductors and/or other components, shaping the thermoplastic elastomer into tubing or other shapes over the pre-assembled conductors and/or components via extrusion or injection molding to produce a shaped elastomer component, assembling the shaped elastomer component with one or more other parts comprising cables, coils, coated cables, or coated coils, and bonding the assembled elastomer component and parts with one or more other components comprising other tubing components, cables, coils, sleeves, electrical pulse generator, defibrillation shock generator, electrodes, sensors, or drug release components.

24. The medical device of claim 1, wherein the thermoplastic elastomer consists of soft segments and hard segments, wherein the soft segments are made of a mixture consisting of polyolefin diols, polyolefin diamine, or a combination thereof, and the hard segment is made of a diisocyanate and a chain extender selected from the group consisting of ethylene glycol, 1,3-propylenediol, 1,4-butanediol, 1,4-hexanediol, 1,4-cyclohexanediol, 1,6-hexanediol, 1,8-octanediol, 1,9-nonanediol, 1,10-decanediol, ethylenediamine, propylenediamine, butylenediamine, hexanediamine, cyclohexanediamine, and mixtures thereof.

* * * * *